United States Patent
Higuchi

(10) Patent No.: US 10,398,594 B2
(45) Date of Patent: Sep. 3, 2019

(54) INTRASCLERAL DRUG DELIVERY DEVICE AND ASSOCIATED METHODS

(75) Inventor: John W. Higuchi, Salt Lake City, UT (US)

(73) Assignee: Aciont, Inc., Salt Lake City, UT (US)

( * ) Notice: Subject to any disclaimer, the term of this patent is extended or adjusted under 35 U.S.C. 154(b) by 228 days.

(21) Appl. No.: 13/113,672

(22) Filed: May 23, 2011

(65) Prior Publication Data

US 2012/0302972 A1    Nov. 29, 2012
US 2014/0031766 A9    Jan. 30, 2014

Related U.S. Application Data

(63) Continuation-in-part of application No. 12/903,837, filed on Oct. 13, 2010, which is a continuation of application No. 11/867,503, filed on Oct. 4, 2007, now Pat. No. 8,480,638.

(51) Int. Cl.
*A61M 35/00*    (2006.01)
*A61F 9/00*    (2006.01)
*A61M 29/00*    (2006.01)

(52) U.S. Cl.
CPC .......... *A61F 9/0026* (2013.01); *A61F 9/0017* (2013.01); *A61F 2250/0068* (2013.01)

(58) Field of Classification Search
CPC ................. A61F 9/0017; A61F 9/0026; A61F 2250/0068
USPC ............................. 604/294, 295, 290, 96.01
See application file for complete search history.

(56) References Cited

U.S. PATENT DOCUMENTS

| | | | |
|---|---|---|---|
| 3,995,635 A | 12/1976 | Higuchi et al. | |
| 5,456,508 A | 10/1995 | Kozar | |
| 5,725,493 A * | 3/1998 | Avery et al. | 604/9 |
| 5,941,583 A | 8/1999 | Raimondi | |
| 6,319,240 B1 | 11/2001 | Beck | |
| 7,621,278 B2 | 11/2009 | Mino Sotelo De Kaspar et al. | |
| 2002/0035345 A1* | 3/2002 | Beck | 604/20 |
| 2006/0088515 A1 | 4/2006 | Higuchi et al. | |
| 2006/0089590 A1* | 4/2006 | Higuchi | A61K 9/0009 604/20 |
| 2007/0093742 A1 | 4/2007 | Higuchi et al. | |
| 2009/0143752 A1 | 6/2009 | Higuchi et al. | |
| 2011/0077582 A1* | 3/2011 | Tuitupou et al. | 604/20 |
| 2011/0268783 A1* | 11/2011 | Shalaby et al. | 424/427 |

* cited by examiner

*Primary Examiner* — Andrew J Mensh
(74) *Attorney, Agent, or Firm* — Thorpe North and Western, LLP; David W. Osborne

(57) ABSTRACT

The present invention provides methods and devices for delivering an active agent into the eye of a subject. In one aspect, for example, the present invention provides an ocular drug delivery device including a housing configured to couple to the eye of the subject and a corneal seal coupled to the housing and positioned in the housing to encircle the cornea during use to form a corneal region, where the housing extends outward from the corneal seal to form a scleral region, and where the scleral region being positioned over the eye's sclera during use. The device further includes an active agent reservoir coupled to the housing and positioned to release active agent into the scleral region and a pressure regulator coupled to the housing that is operable to introduce negative pressure between the housing and the eye. Thus the corneal seal is operable to fluidically isolate the corneal region from the scleral region in response to the negative pressure.

17 Claims, 3 Drawing Sheets

INTRASCLERAL DRUG DELIVERY DEVICE AND ASSOCIATED METHODS

PRIORITY DATA

This application is a continuation-in-part of the U.S. patent application Ser. No. 12/903,837, filed Oct. 13, 2010, which is a continuation of the U.S. patent application Ser. No. 11/867,503, filed on Oct. 4, 2007 now U.S. Pat. No. 8,480,638, each of which are incorporated herein by reference.

FIELD OF THE INVENTION

The present invention relates to systems, methods, and devices for the delivery of an active agent through a region of a subject's ocular tissue. Accordingly, the present invention involves the fields of chemistry, pharmaceutical sciences, and medicine, particularly ophthalmology.

BACKGROUND OF THE INVENTION

Posterior and intermediate eye diseases that require ocular drug delivery to prevent blindness include uveitis, bacterial and fungal endophthalmitis, age-related macular degeneration, viral retinitis, and diabetic retinopathy, among others. For example, the reported incidence of posterior uveitis is more than 100,000 people in the United States. If left untreated, uveitis leads to blindness. It is responsible for about 10 percent of all visual impairment in the U.S. and is the third leading cause of blindness worldwide.

Treatments of intermediate and posterior uveitis are complicated by the inaccessibility of the posterior eye to topically applied medications. Current therapy for intermediate and posterior uveitis requires repeated periocular injections and/or high-dose systemic therapy with corticosteroids. Injections are usually preferred to systemic drug administration because the blood/retinal barrier impedes the passage of most drugs from the systemically circulating blood to the interior of the eye. Therefore large systemic doses are needed to treat intermediate and posterior uveitis, which often result in systemic toxicities including immunosuppression, adrenal suppression, ulcerogenesis, fluid and electrolyte imbalances, fat redistribution and psychological disorders.

Endophthalmitis affects approximately 10,000 people in the United States each year. Endophthalmitis is typically caused by gram-positive bacteria after ocular surgery or trauma, but it can also be fungal or viral in nature. The current method of treating endophthalmitis is direct injection of antimicrobials into the vitreous. Intravitreal injections are necessary because periocular injections and systemic administration do not deliver efficacious amounts of antibiotics to the target sites in the eye. Age-related macular degeneration (AMD) is the leading cause of irreversible loss of central vision in patients over the age of 50. AMD affects more than 15 million people worldwide.

Treatments of posterior eye diseases require intravitreal and periocular injections or systemic drug administration. Systemic administration is usually not preferred because of the resulting systemic toxicity as discussed above. While intravitreal and periocular injections are preferable to systemic administration, the half-life of most injected compounds in the vitreous is relatively short, usually on the scale of just a few hours. Therefore, intravitreal injections require frequent administration. The repeated injections can cause pain, discomfort, intraocular pressure increases, intraocular bleeding, increased chances for infection, and the possibility of retinal detachment. The major complication of periocular injections is accidental perforation of the globe, which causes pain, retinal detachment, ocular hypertension, and intraocular hemorrhage. Other possible complications of periocular injections include pain, central retinal artery/vein occlusion, and intraocular pressure increases. Therefore, these methods of ocular drug delivery into the posterior of the eye have significant limitations and major drawbacks. In addition, injections are very poorly accepted by patients. These methods also involve high healthcare cost due to the involvement of skilled and experienced physicians to perform the injections.

Ocular iontophoresis is a noninvasive technique used to deliver compounds of interest into the interior of a patient's eye. In practice, two iontophoretic electrodes are used in order to complete an electrical circuit. In traditional, transscleral iontophoresis, at least one of the electrodes is considered to be an active iontophoretic electrode, while the other may be considered as a return, inactive, or indifferent electrode. The active electrode is typically placed on an eye surface, and the return electrode is typically placed remote from the eye, for example on the earlobe. The compound of interest is transported at the active electrode across the tissue when a current is applied to the electrodes. Compound transport may occur as a result of a direct electrical field effect (e.g., electrophoresis), an indirect electrical field effect (e.g., electroosmosis), electrically induced pore or transport pathway formation (electroporation), or a combination of any of the foregoing.

One potential problem with present ocular iontophoretic methods and devices concerns the actual delivery, or rather, the non-delivery of the drug into the eye tissue. Because the return electrode is located remote from the eye, various conductive pathways may be formed. Such divergence of the electric current will decrease the efficiency of drug delivery to the target sites in the eye, and as a result, much of the drug may be delivered into the tissues surrounding the eye rather than into the eye per se.

Additionally, despite its apparent advantages, iontophoresis is really just a method of limiting the invasiveness of drug delivery into the eye's interior. Once inside the eye, the pharmacokinetics of water soluble compounds are identical to those following intravitreal injections i.e. their half-lives are on the order of a few hours. Therefore, in many cases, traditional iontophoresis must be repeated as frequently as intravitreal injections, leading to patient inconvenience, increased costs, and increased possibility of untoward effects caused by the iontophoretic treatment itself.

The problem of patient compliance may be compounded by the need to receive daily treatment in a medical facility with high healthcare costs and limited resources and practitioners for treating retinal diseases. Existing ocular iontophoresis systems are not patent-friendly, require multiple parts and assembly to practice, and include either clumsy or complicated procedures. As such, they require the involvement of experienced healthcare professionals to perform the treatments. Paraprofessional and/or in-home self administration use of such devices are precluded by the technical complexity of many existing iontophoretic devices, as well as the costs of expensive dose-controlling equipment. Individuals have a greater tendency to deviate from a medication regimen when required to leave home for medical treatment, particularly when such treatment is frequent.

SUMMARY OF THE INVENTION

The present invention provides methods and devices for the ocular delivering an active agent. In one aspect, for example, the present invention provides an ocular drug delivery device. Such a device can include a housing configured to couple to the eye of the subject and a corneal seal coupled to the housing and positioned in the housing to encircle the cornea during use to form a corneal region, where the housing extends outward from the corneal seal to form a scleral region, and where the scleral region being positioned over the eye's sclera during use. The device further includes an active agent reservoir coupled to the housing and positioned to release active agent into the scleral region and a pressure regulator coupled to the housing that is operable to introduce negative pressure between the housing and the eye. Thus the corneal seal is operable to fluidically isolate the corneal region from the scleral region in response to the negative pressure. Furthermore, the active agent reservoir can be utilized for passive and/or active delivery.

Various pressure regulator configurations are contemplated, and any such configuration that allows negative pressure to be introduced between the eye and the housing is considered to be within the present scope. In one aspect, for example, the pressure regulator is also operable to introduce positive pressure between the housing and the eye to facilitate release of the housing from the eye. In another aspect, the pressure regulator is a vacuum bulb. In yet another aspect, the pressure regulator is removably coupled to the housing.

In one aspect, the device can include a scleral seal coupled to the housing and positioned in the housing to encircle the corneal seal, where the scleral region is between the corneal seal and the scleral seal. In one specific aspect, the scleral seal is an outer edge of the housing. In another specific aspect, the pressure regulator is positioned in the housing to introduce the negative pressure into the scleral region.

In some aspects, the device can include a corneal cover coupled to the housing and extending inward from the corneal seal to completely cover the cornea during use. In one aspect, the pressure regulator is positioned in the housing to introduce the negative pressure into the corneal region.

The present invention additionally provides a method of limiting an active agent from contacting an outer surface of a cornea of an eye during deliver of the active agent to a subject. Such a method can include applying a corneal seal to the eye at least substantially encircling the cornea to form a corneal region, where the corneal seal is coupled to a housing extending outward from the corneal seal over the eye's sclera to form a scleral region. The method also includes applying a negative pressure between the housing and the eye to fluidically isolate the corneal region from the scleral region, and delivering an active agent to the scleral region, whereby the active agent is substantially precluded from the corneal region by the corneal seal. In another aspect, the method can include applying a scleral seal to the eye substantially encircling the corneal seal to form the scleral region, wherein the corneal seal and the scleral seal are coupled together by the housing.

In one specific aspect, the negative pressure is applied between the housing and the eye in the corneal region. In another specific aspect, the negative pressure is applied between the housing and the eye in the scleral region. In yet another specific aspect, the negative pressure is applied between the housing and the eye in both the scleral region and the corneal region. In some aspects the method can additionally include applying a positive pressure between the housing and the eye to facilitate release of the housing from the eye.

The corneal seal can be positioned at various locations on the surface of the eye, provided that the cornea is at least substantially encircled there within. In one aspect, the corneal seal is positioned around the cornea's periphery. In another aspect, the corneal seal is positioned to encircle the cornea at a distance of from about 0.01 mm to about 6.0 mm from the cornea's periphery. In yet another aspect, the corneal seal is positioned to encircle the cornea at a distance of from about 0.01 mm to about 2.0 mm from the cornea's periphery.

Various delivery modalities are also contemplated. For example, in one aspect the active agent is delivered noninvasively. In a more specific aspect, the active agent is passively delivered. In another aspect, the active agent is iontophoretically delivered.

The present invention additionally provides a method of delivering an active agent to an eye of a subject while limiting the active agent from contacting an outer surface of a cornea during delivery. Such a method can include positioning a device as described herein on the eye of the subject, applying negative pressure between the housing and the eye to fluidically isolate the corneal region from the scleral region, and delivering an active agent to the scleral region, whereby the active agent is substantially precluded from the corneal region by the corneal seal.

The particular active agent to be delivered may be a variety of substances depending on the particular treatment to be effected. Such substances may include drugs in various forms, including prodrugs thereof, and sustained release formulations, as required in order to provide convenient and effective minimally invasive or non-invasive delivery. Exemplary active agents are enumerated further herein.

DETAILED DESCRIPTION OF THE INVENTION

Figure 1:
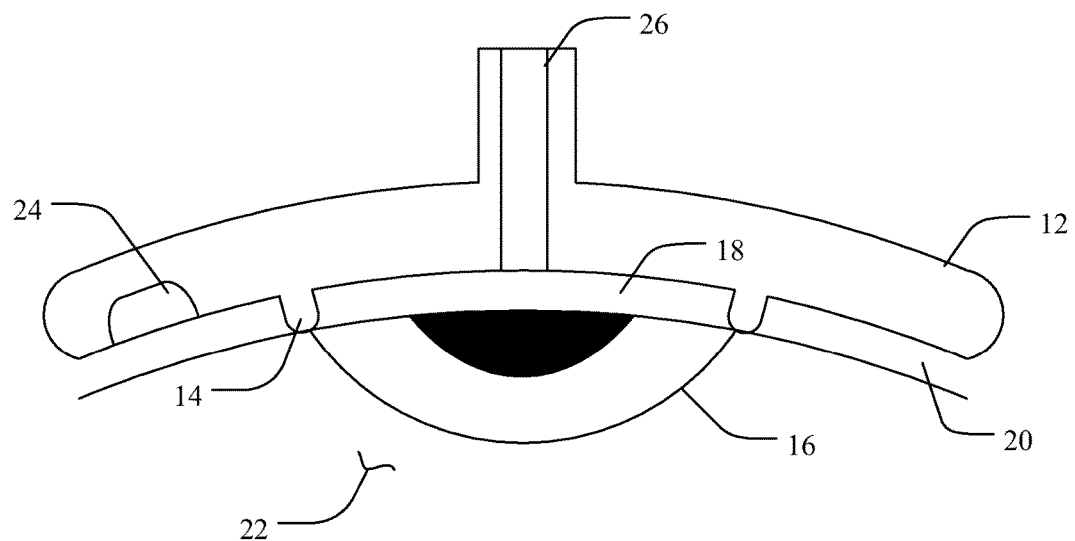
FIG. 1 is a cross section view of an active agent delivery device in accordance with an aspect of the present invention.

Before the present devices and methods for ocular drug delivery are disclosed and described, it is to be understood that this invention is not limited to the particular process steps and materials disclosed herein, but is extended to equivalents thereof, as would be recognized by those ordinarily skilled in the relevant arts. It should also be understood that terminology employed herein is used for the purpose of describing particular embodiments only and is not intended to be limiting.

It must be noted that, as used in this specification and the appended claims, the singular forms "a," "an," and, "the" include plural referents unless the context clearly dictates otherwise. Thus, for example, reference to "a polymer"

includes reference to one or more of such polymers, and "an excipient" includes reference to one or more of such excipients.

Definitions

In describing and claiming the present invention, the following terminology will be used in accordance with the definitions set forth below.

As used herein, "formulation" and "composition" may be used interchangeably herein, and refer to a combination of two or more elements, or substances. In some embodiments a composition may include an active agent, an excipient, or a carrier to enhance delivery or depot formation.

As used herein, "active agent" may be used to refer to an agent or substance that has measurable specified or selected physiologic activity when administered to a subject in a significant or effective amount. It is to be understood that the term "drug" is expressly encompassed by the present definition as many drugs and prodrugs are known to have specific physiologic activities. These terms of art are well-known in the pharmaceutical, and medicinal arts. Examples of drugs useful in the present invention include without limitation, steroids, antibacterials, antivirals, antifungals, antiprotozoals, antimetabolites, immunosuppressive agents, VEGF inhibitors, ICAM inhibitors, antibodies, protein kinase C inhibitors, chemotherapeutic agents, neuroprotective agents, nucleic acid derivatives, aptamers, proteins, enzymes, peptides, and polypeptides.

As used herein "prodrug" refers to a molecule that will convert into a drug (its commonly known pharmacological active form). Prodrugs themselves can also be pharmacologically active, and therefore are also expressly included within the definition of an "active agent" as recited above. For example, dexamethasone phosphate can be classified as a prodrug of dexamethasone, and triamcinolone acetonide phosphate can be classified as a prodrug of triamcinolone acetonide.

As used herein, "effective amount," and "sufficient amount" may be used interchangeably and refer to an amount of an ingredient which, when included in a composition, is sufficient to achieve an intended compositional or physiological effect. Thus, a "therapeutically effective amount" refers to a non-toxic, but sufficient amount of an active agent, to achieve therapeutic results in treating a condition for which the active agent is known to be effective. It is understood that various biological factors may affect the ability of a substance to perform its intended task. Therefore, an "effective amount" or a "therapeutically effective amount" may be dependent in some instances on such biological factors. Further, while the achievement of therapeutic effects may be measured by a physician or other qualified medical personnel using evaluations known in the art, it is recognized that individual variation and response to treatments may make the achievement of therapeutic effects a subjective decision. The determination of an effective amount is well within the ordinary skill in the art of pharmaceutical sciences and medicine. See, for example, Meiner and Tonascia, "Clinical Trials: Design, Conduct, and Analysis," *Monographs in Epidemiology and Biostatistics, Vol.* 8 (1986), incorporated herein by reference.

As used herein, "sclera" refers to the sclera tissue in the eye or the conjunctiva between the limbus and the fornix on the surface of the eye, which is the white part of the eye. In some aspects "sclera" can be used in referring to other eye tissues.

As used herein, "eye" refers to the globe of the eye. As such, delivery of an active agent into the eye refers to delivery of the active agent into the globe of the eye itself.

As used herein, "subject" refers to a mammal that may benefit from the administration of a composition or method as recited herein. Examples of subjects include humans, and may also include other animals such as horses, pigs, cattle, dogs, cats, rabbits, and aquatic mammals.

As used herein, "administration," and "administering" refer to the manner in which an active agent, or composition containing such, is presented to a subject. As discussed herein, the present invention is primarily concerned with noninvasive delivery such as passive delivery or iontophoretic delivery, especially with ocular delivery.

As used herein, "noninvasive" refers to a form of administration that does not rupture or puncture a biological membrane or structure with a mechanical means across which a drug or compound of interest is being delivered. A number of noninvasive delivery mechanisms are well recognized in the transdermal arts such as patches, and topical formulations. Many of such formulations may employ a chemical penetration enhancer in order to facilitate noninvasive delivery of the active agent. Additionally, other systems or devices that utilize a non-chemical mechanism for enhancing drug penetration, such as iontophoretic devices are also known. "Minimally invasive" refers to a form of administration that punctures a biological membrane or structure but does not cause excessive discomfort to the subjects and severe adverse effects. Examples of "minimally invasive" drug delivery are microneedle, laser, or heat punctuation in transdermal delivery and periocular injections in ocular delivery.

As used herein, the term "outward" refers to a direction extending away from the center of the cornea. Thus extending "outward" from the corneal seal is intended to describe a region extending from the side of the corneal seal opposite to the center of the cornea.

As used herein, "depot" refers to a temporary mass inside a biological tissue or system, which includes a drug that is released from the mass over a period of time. In some aspects, a depot may be formed by the interaction of an active agent with a depot forming agent, such as a complexing ion which will form an active agent complex that is less soluble than the active agent by itself, and thus precipitate in-vivo.

As used herein, the term "body surface" refers to an outer tissue surface of the subject such as tissue surfaces encountered in ocular and transdermal delivery, or mucosal tissues lining a body cavity such as the mouth for buccal delivery or vaginal tract for vaginal delivery. The term "skin" refers to an outer tissue surface of the subject. It is therefore intended that skin also refer to mucosal and epithelial tissues, as well as the outer surfaces of the eye.

As used herein, the terms "anode" and "cathode" refer to the electrical polarity of an electrode. The terms "anode" and "cathode" are well known in the art. It should be noted, however, that in some aspects these descriptive terms may be transitory. When using alternating current, for example, two electrodes will alternate between anode and cathode as the current alternates in electrical polarity.

As used herein, the term "reservoir" refers to a body, a lumen, or a mass that may contain an active agent, a depot forming agent, secondary compound, or other pharmaceutically useful compound or composition. As such, a reservoir may include any structure that may contain a liquid, a gelatin, a semi-solid, a solid or any other form of active agent or secondary compound known to one of ordinary skill in the art. In some cases, an electrode may be considered to be a reservoir.

As used herein, the term "contact lens" refers to a lens sized to fit approximately over the cornea of the eye.

As used herein, the term "scleral lens" refers to a lens sized to cover and extend beyond the cornea across at least a portion of the sclera of the eye.

As used herein, the term "active electrode" refers to an electrode utilized to iontophoretically deliver an active agent.

As used herein, the term "passive electrode" refers to an electrode that is used to complete an electrical circuit without delivering a compound or substance to a subject.

As used herein, the term "return electrode" refers to an electrode utilized to complete an electrical circuit for active electrode. In one aspect, a return electrode may be an active electrode used to deliver a secondary compound, such as an active agent, a depot forming agent, etc. In another aspect, a return electrode may be a passive electrode.

As used herein, the term "self-contained" refers to a device that contains therein, or substantially therein, all the components required for use. For example, a self-contained iontophoretic device may contain active agents, reservoirs, electrodes, power supplies, etc., within a single housing.

As used herein, the term "reacting" refers to any force, change in environmental conditions, presence or encounter of other chemical agent, etc. that alters the active agent. For example, "reacting" between the active agent and the depot forming agent can be physical or chemical interactions.

As used herein, the term "precipitate" refers to anything less than fully solubilized. As such, a precipitate can include not only crystals, but also gels, semi-solids, increased molecular weight, etc.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc.

This same principle applies to ranges reciting only one numerical value. Furthermore, such an interpretation should apply regardless of the breadth of the range or the characteristics being described.

The Invention

The present disclosure relates to devices for the delivery of an active agent into the eye of a subject, including various methods associated with such devices. The inventors have discovered that ocular delivery of an active agent can be facilitated and/or enhanced through the use of a vacuum applied between the device and the surface of the eye. This vacuum force can function to improve contact between the device and the eye, isolate certain eye structures from contact with the active agent, and preclude contact between the active agent and lachrymal fluid, among other things. By applying a vacuum force between the eye and the device, the device housing is brought into a more intimate contact with the surface of the eye. Such an improved contact can have a variety of beneficial effects pertaining to ocular drug delivery, and such benefits can vary depending on the design of the device and the location of the vacuum within the device and relative to the surface of the eye. For example, a vacuum between the device and the eye can cause a tight adherence there between. Such a tight adherence or "gripping" of the eye surface by the device maintains the active agent reservoir at a distinct location with respect to the eye. In some cases, eye tissue associated with a reservoir can become "primed" and thus more readily pass active agent there through. Accordingly, maintaining the reservoir at a distinct location can enhance active agent delivery. Additionally, in those aspects where a drug depot is delivered into the eye, maintaining the active agent and/or depot forming agent reservoir at a distinct location allows the formation of the depot at a correspondingly distinct location within the eye. Moving the reservoir(s) relative to the eye during delivery can cause a drug depot to form having a greater surface area than intended, and thus a greater active agent release from the depot that expected.

As another example, when a housing is placed upon the eye, air pockets can be present along the eye/device interface. This air can, in some cases, increase the required travel distance for an active agent to move to and contact the eye surface during delivery. In addition to increasing travel or diffusion distance, air situated between the eye and the device can greatly slow or even halt the movement of the active agent through the surrounding fluid. A vacuum force pulls the housing toward the eye, thus displacing a portion of the fluid and/or the trapped air. In those cases where the active agent is delivered from a portion of the housing subject to the vacuum, air pockets are eliminated or substantially reduced by the vacuum, and thus increased mobility of the active agent is achieved. In those cases where the active agent is delivered from a portion of the housing that is not subject to the vacuum (i.e. separated by a barrier structure), air pockets can be drawn to the vacuumed portion as the barrier seals and can be pressed from the interface as the housing is pulled toward the eye.

The inventors have also discovered that ocular damage and/or side effects such as edema may occur when the cornea is exposed to various active agents and/or components of the active agent formulation at certain (particularly high) concentrations. At lower concentrations of the active agent formulation, some irritation to the cornea or patient discomfort during treatment can occur, as the cornea is a highly sensitive tissue. As such, it can be beneficial to preclude exposure of these active agents and components to corneal tissues during drug delivery. This can be accomplished by providing a seal between the active agent reservoir and the cornea during use. The vacuum, whether it is applied at the cornea, at the active agent reservoir, or both, will function to seal the corneal region from contact with the active agent formulation. Additionally, in some cases direct physical contact between the device and the cornea can cause damage and/or side effects. Thus in some aspects, sealing the device at the corneal seal can protect the cornea from physical contact, thus reducing the possibility of corneal damage. Furthermore, when active agent delivery to posterior structures of the eye are desired and thus delivery of the active agent through the sclera is desired, limiting active agent exposure to surface areas of the cornea can be beneficial.

Accordingly, in one aspect of the present invention, an ocular drug delivery device is provided. As is shown in FIG. 1, such a device can include a housing 12 configured to couple to the eye of the subject, and a corneal seal 14 coupled to the housing and positioned in the housing to encircle the cornea 16 during use to form a corneal region 18. The corneal region 18 is thus an area that is sealed and prevented from being contacted by significant amounts of the active agent formulation. The housing 12 extends outward from the corneal seal 14 to form a scleral region 20, where the scleral region is positioned over the eye's sclera 22 or conjunctiva during use. The device also includes an active agent reservoir 24 coupled to the housing 12 and positioned to release active agent into the scleral region 20, and a pressure regulator 26 coupled to the housing 12 that is operable to introduce negative pressure (i.e. a vacuum) between the housing and the eye. The corneal seal 14 is operable to fluidically isolate or substantially fluidically isolate the corneal region 18 from the scleral region 20 in response to the negative pressure. Additionally, as the negative pressure is applied the corneal seal provides an initial contact or gripping point that fixed the position of the device as it seals. The location of the strongest contact pressure will thus occur along the corneal seal. This is contrary to devices lacking such a corneal seal that can begin to seal in an arbitrary fashion, and thus may not adhere in the intended position. For configurations where the vacuum is applied at the center of the cornea, designs lacking a corneal seal may begin to adhere from the periphery or a portion of the periphery inward in an arbitrary manner. Designs having a corneal seal will grip the eye and adhere around the seal with a vacuum being formed within the sealed region in a predictable manner. As the seal is formed, air pockets are sucked from the corneal region into the pressure regulator as opposed to being forced away from the pressure regulator due to the movement of the housing in response to the negative pressure.

Various designs of corneal seals are contemplated, and any such design that is capable of fluidically isolating or substantially fluidically isolating the corneal region from the scleral region is considered to be within the present scope.

In one aspect, for example, the corneal seal is an annular or elliptical seal surrounding or substantially surrounding the cornea. The actual shape and/or geometry of the corneal seal can vary widely, and it should be understood that any corneal seal configuration that surrounds the cornea and provides fluidic isolation from the scleral region is considered to be within the present scope. The corneal seal can be a projection or extension of the housing material, or it can be formed separately and attached thereto. When positioning the device in the eye, the corneal seal can be initially contact the eye and allow for proper positioning prior to the introduction of the negative pressure between the device and the eye surface. Once the device has been positioned, the negative pressure can be introduced to cause the housing to adhere to the surface of the eyeball, thus fluidically isolating the corneal region from the scleral region.

The corneal seal is thus sized and positioned in the housing to encircle or substantially encircle the cornea during use. The corneal seal can be sized and positioned at any location on the eye surface that allows the cornea to be encircled or substantially encircled, provided a sufficient scleral region is available from which to deliver the active agent. In one aspect, the corneal seal is positioned around the cornea's periphery. In another aspect, the corneal seal is positioned to encircle the cornea at a distance of from about 0.01 mm to about 6.0 mm from the cornea's periphery. In yet another aspect, the corneal seal is positioned to encircle the cornea at a distance of from about 0.01 mm to about 2.0 mm from the cornea's periphery. Additionally, in one aspect the corneal seal can be a circular or annular ring. In another aspect, the corneal seal can be an elliptical or semielliptical ring. It is contemplated that the corneal seal can be of any shape or configuration that limits or substantially limits contact between the cornea and the active agent, and any such configuration or shape is considered to be within the present scope.

Numerous configurations of the housings of the devices of the present invention are contemplated, for both single-use and multiple-use devices. In one aspect for example, the housing can be configured to allow the eyelids of the subject to close substantially completely thereover. In other words, when the device is in contact with the eye, the subject may be able to blink in a fairly normal fashion. In one aspect, such a device can be configured to resemble a contact lens or a scleral lens. Additionally, for those aspects whereby the negative pressure is introduced into the corneal region, a portion of housing can be disposed over the corneal region to provide the vacuum seal. Such a corneal cover can also extend the potential duration of drug delivery by protecting the cornea from drying out and becoming uncomfortable for the subject. In one aspect, the housing can be configured to conform to the surface of the eyeball. Such a conformation in shape can facilitate the sealing of the corneal seal once the vacuum force is applied.

In another aspect, the housing can be configured to be substantially self-contained. Such a self-contained device would contain all the components used in the delivery of the active agent into the eye. In the case of iontophoretic delivery, for example, the power supply, electrodes, and conductive connections there between are contained in the device. In this manner, the device allows simple insertion onto the surface of the eye, and can facilitate substantially normal eye closure and blinking during use. This is particularly advantageous for ocular iontophoresis as it provides an easy-to-use all-in-one device that improves patient compliance, especially, when multiple applications are required. In some aspects, the power supply can be located remotely however.

Various materials are contemplated for use as the housing that can securely contain the various components of the device. In the case of iontophoretic devices, the housing materials or at least a portion of the housing materials associated with the electrodes should have dielectric properties sufficient to maintain these components in electrical isolation. It may be additionally beneficial to utilize materials that provide some level of physical flexibility to avoid damage or irritation to the eye surface. Any material having properties beneficial to the construction of such a device would be considered to be within the scope of the present invention. For example, the housing material may include, without limitation, plastics, metals, composites, Teflon, nylons, polyesters, polyurethanes, polyethylenes, polycarbonates, and the like. Materials such as metals may be utilized that are conductive, and thus would need have dielectric materials incorporated therein in order to maintain electrical isolation between various components of the device if used in an iontophoretic device.

Figure 2:
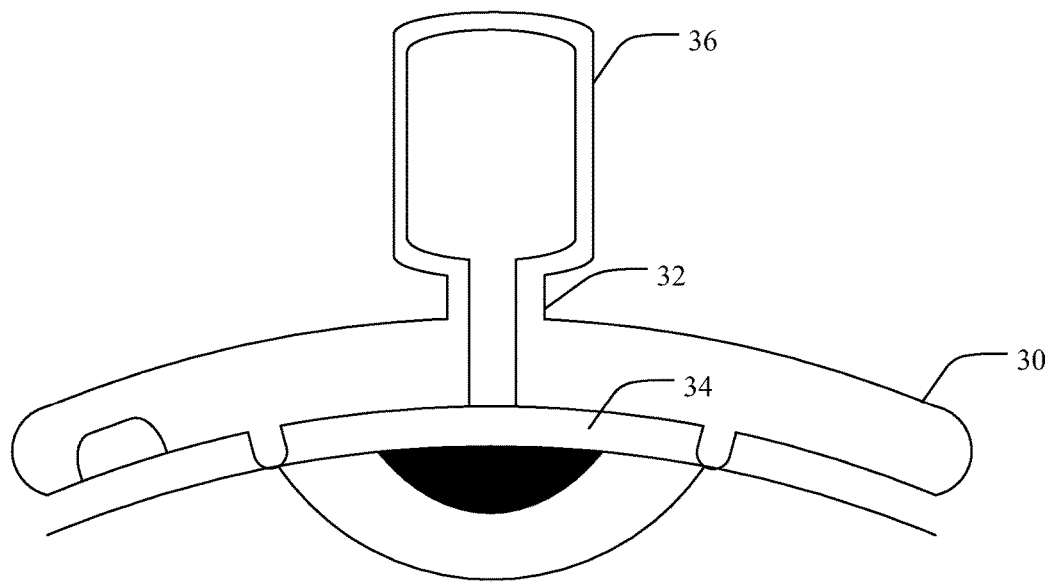
FIG. 2 is a cross section view of an active agent delivery device in accordance with another aspect of the present invention.

The housing can also include a pressure regulator to create negative pressure between the device and the surface of the eye as has been described. The negative pressure should be strong enough to hold the device in place during blinking. The negative pressure can be introduced in the corneal region, the scleral region, or in both the corneal and scleral regions. As is shown in FIG. 2, for example, the housing 30 can include a pressure regulator 32 associated therewith. In this aspect, the pressure regulator 32 is operable to deliver negative or positive pressure to the corneal space 34. Regardless of location, the pressure regulator can be of various configurations. For example, in one aspect, the pressure regulator can be a port or coupling for the attachment of a pressure generating device such as a syringe (not shown). In another aspect, as is shown in FIG. 2, the pressure regulator 32 includes an attached pressure bulb 36 used to generate positive and negative pressure by squeezing. Thus by squeezing and releasing the bulb, negative pressure is introduced into the corneal region. Further squeezing of the bulb can generate positive pressure to allow release of the device from the eye. Thus in this case, the bulb can be made having enough internal volume to seal the device with negative pressure and unseal the device following further squeezing. Whether or not a pressure bulb is used, the pressure regulator can be configured for use as a handle to facilitate manipulation of the device before, during, and after positioning on the eye. In some aspects, a flow regulator or valve can be associated with the pressure regulator in order to control the flow of positive or negative pressure. In another aspect, the pressure regulator can be positioned in the housing at a location that is off-center relative to the center of the cornea in order to allow the subject to more easily blink or see through the device (not shown).

Figure 3:
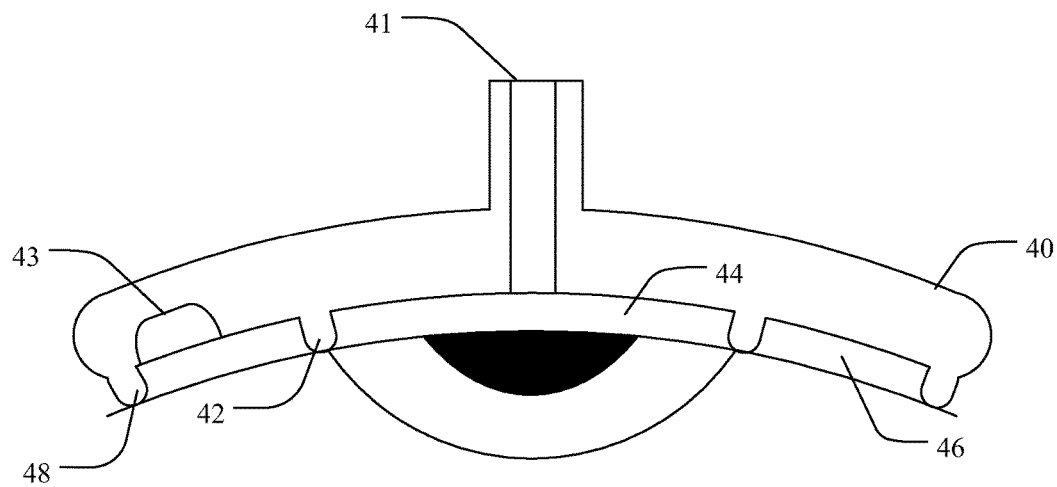
FIG. 3 is a cross section view of an active agent delivery device in accordance with yet another aspect of the present invention.

In various aspects of the present invention, a scleral seal can also be positioned on the housing to provide a secondary seal. The scleral seal can encircle the corneal seal and create a sealable scleral region there between into which the active agent can be delivered for subsequent movement into the eye. This configuration can be beneficial for designs where the scleral region is under negative pressure, or where it is desirable to preclude lachrymal fluids from entering the scleral region. As such, the negative pressure can be applied between the housing and the eye in the scleral region, the corneal region, or both. As is shown in FIG. 3, the device housing 40 includes a corneal seal 42 to fluidically separate the corneal region 44 from the scleral region 46, and a scleral seal 48 to further seal the scleral region 46. A pressure regulator 41 is shown for introducing negative pressure into the corneal region 44. As with the corneal seal, the scleral seal can be an extended or protruded section of the housing, or it can be a separate material that is subsequently associated with the housing. Thus active agent is released from the active agent reservoir 43 into the scleral region 46 and maintained there during delivery into the eye. Additionally, in some aspects the scleral seal can be an outer edge of the housing, provided proper sealing can occur in response to negative pressure.

Figure 4:
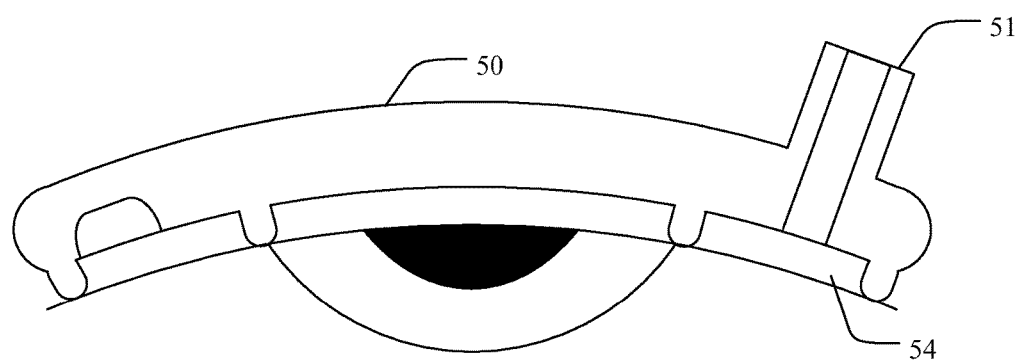
FIG. 4 is a cross section view of an active agent delivery device in accordance with a further aspect of the present invention.

In another aspect, as is shown in FIG. 4, the housing 50 can include a pressure regulator 51 operable to deliver negative or positive pressure to the scleral region 54. Other than the placement of the pressure regulator, FIG. 4 is similar in structure to FIG. 3. When negative pressure is applied to the scleral region, the housing is adhered to the eye surface and the corneal seal precludes contact between the active agent formation and the cornea. In other aspects it is also contemplated that the pressure regulator can be at least partially coupled through the housing to both the scleral and corneal regions (not shown). In such cases, the pressure regulator can be located anywhere on the housing with pressure delivering channels connecting both corneal and scleral regions. It is also contemplated that a pressure regulator functionally coupled to only the corneal region can be located in the housing over the scleral region, and alternatively that a pressure regulator functionally coupled to only the scleral region can be located in the housing over the corneal region. Furthermore, in some aspects an additional seal can be present to separate the negative pressure introduced into the scleral region from the active agent reservoir.

Figure 5:
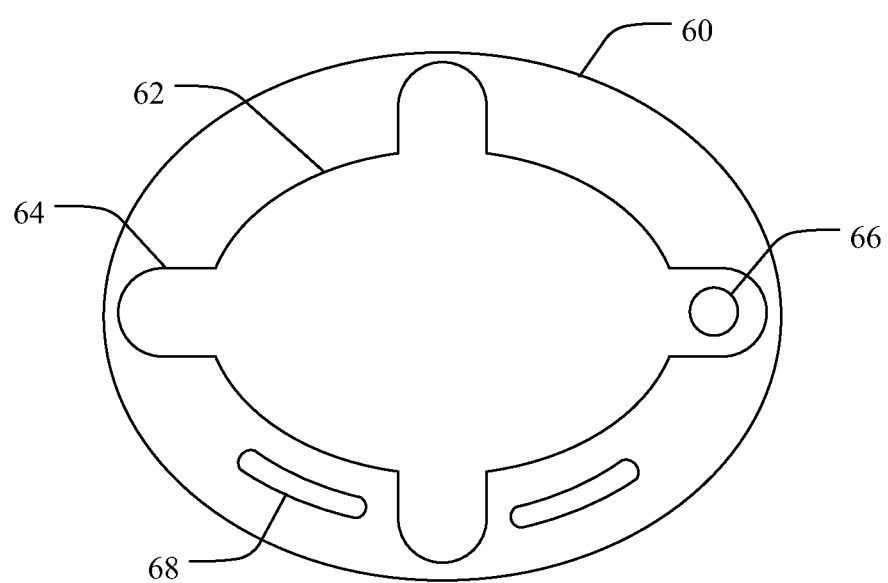
FIG. 5 is a top view of an active agent delivery device in accordance with a further aspect of the present invention.

As has been described, the device can be configured so as to minimize obstructing the vision of a subject during active agent delivery. In one aspect, as is shown in FIG. 5 for example, a device can have a housing 60 and a corneal seal 62. One or more corneal seal extensions 64 can be extended away from the cornea for the inclusion of a pressure regulator 66. In this way the pressure regulator 66 is positioned out of the visual field of the subject, thus minimizing visual obstruction. Note that the active agent reservoir(s) 68 are located in the housing 60 on the outside of the corneal region 62, and are thus isolated from the cornea. It is also contemplated that a single corneal extension can be used, thus allowing a more continuous active agent reservoir surrounding a portion to substantially all of the corneal seal.

As has been described, at least one active agent reservoir is associated within the housing in a position to deliver at least one active agent and in some cases at least one secondary compound such as a depot forming agent into the eye. The reservoirs according to aspects of the present invention are thus designed to hold an active agent or other secondary compound prior to and during administration into the eye of a subject. In one aspect, a reservoir can be a distinct compartment, having a lumen for holding an active agent or other secondary compound to be delivered. A reservoir can be a recessed portion of the housing, a separate structure coupled to the housing, or any other reservoir configuration capable of containing an active agent or a secondary compound. In some aspects, the reservoir can be located at a single discrete location in the housing. As one non-limiting example, the reservoir can be positioned in the housing to only contact the sclera in the lower cul-de-sac of the eye. As another example, the reservoir can be positioned in the housing to only contact the sclera in the upper cul-de-sac of the eye. In other aspects, the reservoir can be located across a much broader area of the scleral region. In one non-limiting example, the reservoir can be an annular ring that encircles or substantially encircles the cornea within the scleral region. In another example, the reservoir can have an arc shape, and thus partially encircle the cornea in the scleral region. Such would be the case for an arc-shaped reservoir partially encircling the cornea within the lower cul-de-sac in the scleral region. Additionally, in one aspect the active agent reservoir surface area can include substantially all of the area of the scleral region. In another aspect, the active agent reservoir has a surface area that is less than or equal to about 75% of the surface area of the scleral region. In yet another aspect, the active agent reservoir has a surface area that is less than or equal to about 50% of the surface area of the scleral region. In a further aspect, the active agent reservoir has a surface area that is less than or equal to about 25% of the surface area of the scleral region. In yet a further aspect, the active agent reservoir has a surface area that is less than or equal to about 10% of the surface area of the scleral region.

Additionally, such a reservoir can contain at least one access port to allow the reservoir to be filled, either before, during, or after contact with the eye surface of the subject. Such a configuration can allow the reservoir to be filled during use as the agent within is depleted. In another aspect, a reservoir can be filled during manufacture of the device with an active agent or other secondary compound to be delivered, particularly in those aspects where the device is intended for a single use. Various reservoir materials are known to those skilled in the art, and all are considered to be within the scope of the present invention. Additionally, the active agent or secondary compound can be included in the reservoir in any form, including, without limitation, a liquid, gelatinous, semi-solid, or solid form. In another aspect the reservoir can consist of a portion of the active electrode, such that an active agent or secondary compound is delivered from the electrode when electrical current is introduced.

The devices of the present invention, and thus the active agent reservoirs themselves, can be configured for active or passive delivery. Passive delivery of an active agent is accomplished by releasing the active agent into the scleral region and allowing passive diffusion to move the active agent into the eye. The active agent can be allowed to freely diffuse throughout the scleral region, or it can be contained in a localized region in proximity to the reservoir. In some aspects the active agent can be formulated for passive delivery using various permeation enhancers and/or passive delivery techniques. Further details regarding passive delivery can be found in U.S. patent application Ser. No. 11/999,266, filed on Dec. 3, 2007, which is incorporated herein by reference.

Active delivery of an active agent can be accomplished by a variety of techniques, including, without limitation, iontophoresis, sonophoresis, and the like. In the case of iontophoresis, for example, the active agent reservoir (and in some cases the secondary agent reservoir) is configured to receive electrical current from an active electrode to thus iontophoretically deliver an active agent or other compound therefrom. A return or inactive electrode is electrically coupled to the subject to complete the electrical circuit. The return electrode can be located either on the surface of the eye or at a location remote from the eye such as the earlobe. In some aspects, the return electrode can be an "active" electrode and be associated with a reservoir to deliver a secondary agent or compound. In such cases, the return electrode and the associated reservoir are likely situated on the surface of the eye. Further details regarding iontophoretic delivery can be found in U.S. patent application Ser. No. 11/414,134, filed on Apr. 27, 2006, which is incorporated herein by reference.

Various placement configurations of electrode/reservoir assemblies are contemplated. For example, in many cases side-by-side electrode/reservoir assembly configurations may be beneficial. Such a configuration may allow effective iontophoresis at a target location while minimizing the extent of the movement of the electrical current in other parts of the body. This is particularly beneficial when administering an active agent to sensitive areas such as the eye, where potential adverse effects may be caused by excessive electrical current passing through particularly sensitive tissues such as the retina in the back of the eye, the optic nerve, etc. Numerous placement configurations are possible, and those discussed herein should not be seen as limiting. In one aspect the electrode/reservoir assemblies can be located side-by-side on the conjunctiva and sclera. In another aspect, one electrode/reservoir assembly may be located in the inferior cul-de-sac and the other electrode/reservoir assembly can be located in the superior cul-de-sac. The active agent can be delivered to various tissue regions depending on the relative locations of the electrode/reservoir assemblies, such as the sclera, conjunctival, subconjuctival space, ciliary body, choroids, retina, anterior chamber, vitreous, etc. The preferred site may depend on the site of drug action in the eye to provide a pharmacological effect.

Prior methods of iontophoretic delivery of an active agent to the eye often locate return electrodes remote from the eye. While such embodiments are considered to be within the scope of the present invention, such configurations are inconvenient and allow various conductive pathways to be formed across the tissues surrounding the eye rather than focused only in the eye per se. Placing both the active and return electrodes in association with the surface of the eye can facilitate the passage of electrical current transsclerally into the eye under the electrodes, particularly when current movement across the surface of the eye is limited. In one aspect, the electrodes can be respectively configured on the surface of the eye such that an electrical circuit is completed substantially within the eye of the subject. In other words, the current between the electrodes passes predominantly through the eyeball tissues rather than into or through the connective tissues surrounding the eye. The active and return electrodes can directly contact the surface of the eye, or they can contact the surface of the eye through an intermediate material or reservoir that is part of the device. In either case, such a "direct" contact between the electrodes and the eye surface may facilitate the focusing of electrical current within the eye.

The relative spacing or the inter-electrode distance between the electrodes can play an important role in determining where an active agent is localized in the eye upon delivery. As such, in accordance with one aspect of the present invention, the electrodes can be spaced at an inter-electrode distance that controls the depth and extent of penetration of the active agent within the eye. Such a spacing can focus the electric field more effectively within the eye, thus more effectively delivering the active agent. Increasing the inter-electrode distance will generally cause current to flow deeper into the eye, thus iontophoretically delivering the active agent deeper. Small inter-electrode distances will cause a more superficial delivery of active agent into the eye. Thus, by altering the physical locations of each of the electrodes relative to one another, and thus the inter-electrode distance between them, the active agent can be delivered to particular regions of the eye at specific depths. As such, the inter-electrode distance may vary depending on the intended delivery location. In one aspect of the present invention, however, the inter-electrode distance may be less than about 40.0 mm. In yet another aspect, the inter-electrode distance may be from about 1 mm to about 10 mm. In a further aspect, the inter-electrode distance may be from about 0.3 mm to about 4 mm.

The active and return electrodes pass current due to a potential difference established there between by a power source. The current acts to move an active agent iontophoretically in a direction that is dependent on the charge characteristics of the active agent and the charge orientation of the potential difference between the electrodes. An active electrode, whether it be an anode or a cathode, is designed to deliver electrical current across an associated reservoir to iontophoretically deliver the active agent located therein. As has been described, in one aspect, one electrode can be an active electrode and the other electrode can be a return electrode for merely completing the electrical circuit. For example, the active electrode can be an anode and the return electrode can be a cathode, or vice versa. In another aspect, one both the anode and the cathode can each have an associated reservoir for the delivery of compounds. The compounds can be the same or different, depending on the intended use and/or configuration of the device. In those aspects where the compounds are different, both compounds can be active agents, or one compound can be an active agent and one compound can be a secondary compound or agent that may or may not have a direct therapeutic effect. One example of such a compound is a depot forming agent. The anode and the cathode can be of the same or different size relative to each other. Also, the surface area of one or both electrodes can be configured to modify their respective current densities when in use.

The present invention also includes methods that involve delivering an active agent into the eye of a subject. In one aspect, for example, a method of limiting an active agent from contacting an outer surface of a cornea of an eye during delivery of the active agent to a subject is provided. Such a method can include applying a corneal seal to the eye at least substantially encircling the cornea to form a corneal region, wherein the corneal seal is coupled to a housing extending outward from the corneal seal over the eye's sclera to form a scleral region. A negative pressure is applied between the housing and the eye to fluidically isolate the corneal region from the scleral region, and an active agent is delivered to the scleral region. Thus the corneal seal substantially precludes the active agent from entering the corneal region. In another aspect, the method can further include applying a scleral seal to the eye substantially encircling the corneal seal to form the scleral region, wherein the corneal seal and the scleral seal are coupled together by the housing. Such a method can be performed to administer an active agent into the eye to treat various ocular and/or systemic medical conditions.

Though numerous conditions would benefit from the methods and devices of the present invention, they are particularly well suited for the treatment of ocular diseases such as direct, combinatory, and adjunctive therapies. This is because of the relatively high permeability of the eye tissues and the large aqueous compartments in the eye. Examples of eye diseases include without limitation, macular edema, age related macular degeneration, anterior, intermediate, and posterior uveitis, HSV retinitis, diabetic retinopathy, bacterial, fungal, or viral endophthalmitis, eye cancers, glioblastomas, glaucoma, and glaucomatous degradation of the optic nerve.

Accordingly, a wide range of active agents may be used in the present invention as will be recognized by those of ordinary skill in the art. In fact, any agent that may be beneficial to a subject when administered ocularly may be used. Examples of the active agents that may be used in the treatment of various conditions include, without limitation, analeptic agents, analgesic agents, anesthetic agents, antiasthmatic agents, antiarthritic agents, anticancer agents, anticholinergic agents, anticonvulsant agents, antidepressant agents, antidiabetic agents, antidiarrheal agents, antiemetic agents, antihelminthic agents, antihistamines, antihyperlipidemic agents, antihypertensive agents, anti-infective agents, antiinflammatory agents, antimigraine agents, antineoplastic agents, antiparkinsonism drugs, antipruritic agents, antipsychotic agents, antipyretic agents, antispasmodic agents, antitubercular agents, antiulcer agents, antiviral agents, anxiolytic agents, appetite suppressants, attention deficit disorder and attention deficit hyperactivity disorder drugs, cardiovascular agents including calcium channel blockers, antianginal agents, central nervous system ("CNS") agents, beta-blockers and antiarrhythmic agents, central nervous system stimulants, diuretics, genetic materials, hormonolytics, hypnotics, hypoglycemic agents, immunosuppressive agents, muscle relaxants, narcotic antagonists, nicotine, nutritional agents, parasympatholytics, peptide drugs, psychostimulants, sedatives, steroids, smoking cessation agents, sympathomimetics, tranquilizers, vasodilators, β-agonists, and tocolytic agents, and mixtures thereof.

Additionally, further examples of active agents may include steroids, aminosteroids, antibacterials, antivirals, antifungals, antiprotozoals, antimetabolites, VEGF inhibitors, ICAM inhibitors, antibodies, protein kinase C inhibitors, chemotherapeutic agents, immunosuppressive agents, neuroprotective agents, analgesic agents, nucleic acid derivatives, aptamers, proteins, enzymes, peptides, polypeptides and mixtures thereof. Specific examples of useful antiviral active agents include acyclovir or derivatives thereof.

Specific examples of active agents may also include hydromorphone, dexamethasone phosphate, amikacin, oligonucleotides, $F_{ab}$ peptides, PEG-oligonucleotides, salicylate, tropicamide, methotrexate, 5-fluorouracil, squalamine, triamcinolone acetonide, diclofenac, combretastatin A4, mycophenolate mofetil, mycophenolic acid, and mixtures thereof.

Under a number of circumstances, the active agent used may be a prodrug, or in prodrug form. Prodrugs for nearly any desired active agent will be readily recognized by those of ordinary skill in the art. Additionally, prodrugs with high electromobility which metabolize into drugs with a low aqueous solubility may be beneficial. In this case, an electrically mobile prodrug of a low solubility drug in iontophoresis can be used to create a sustained release system in the eye. Because the prodrug has high electromobility, it is effectively delivered into the eye. The prodrug then converts into the low solubility drug in the eye and the insoluble drug precipitates in the eye. The drug in solid state in the eye will be slowly released into the eye and provide an ocular sustained release condition.

Though any prodrug would be considered to be within the scope of the present invention, examples may include the derivatives of steroids, antibacterials, antivirals, antifungals, antiprotozoals, antimetabolites, VEGF inhibitors, ICAM inhibitors, antibodies, protein kinase C inhibitors, chemotherapeutic agents, immunosuppressive agents, neuroprotective agents, analgesic agents, nucleic acid derivatives, aptamers, proteins, enzymes, peptides, polypeptides, and mixtures thereof. One specific example of a steroid derivative may include triamcinolone acetonide phosphate or other derivatives of triamcinolone acetonide, dexamethasone phosphate. For example, it may be preferable to label a steroid with one or more phosphate, sulfate, or carbonate functional groups, so the prodrug can be effectively delivered into the eye and form a complex with the precipitating ion.

In some cases, ocular treatment may be hampered by the in-vivo movement/clearance of the active agent in the eye. It is therefore contemplated that various means for restricting or slowing such movement may improve the effectiveness of the active agent therapy. In one aspect, the in-vivo movement may be restricted by constriction of the blood vessels exiting an area in which the active agent is being delivered or precipitated. Such constriction may be induced by the administration of a vasoconstricting agent. Such a vasoconstrictor may be administered actively by iontophoretic or other means, or it may be delivered passively. Specific non-limiting examples of vasoconstricting agents may include α-agonists such as naphazoline, and tetrahydrozoline, sympathomimetics such as phenylethylamine, epinephrine, norepinephrine, dopamine, dobutamine, colterol, ethylnorepinephrine, isoproterenol, isoetharine, metaproterenol, terbutaline, metearaminol, phenylephrine, tyramine, hydroxyamphetamine, ritrodrine, prenalterol, methoxyamine, albuterol, amphetamine, methamphetamine, benzphetamine, ephedrine, phenylpropanolamine, methentermine, phentermine, fenfluramine, propylhexedrine, diethylpropion, phenmetrazine, and phendimetrazine. Vasoconstricting agents can be administered either before or concurrently with the administration of the active agent. Though administration of the vasoconstrictor may occur following administration of the active agent, the results may be less effective than prior or concurrent administration. Additionally, in some aspects, the vasoconstricting agent may have the same polarity as the active agent and administered concurrently with the active agent. Similarly, the vasoconstricting agent may have the opposite polarity as active agent, and thus be administered from a return electrode.

It may also be beneficial for the application site to be sealed with a sealant following delivery of the active agent. This procedure may protect the tissue in which iontophoretic administration occurred. Sealants may include any known to one of ordinary skill in the art, including gels, glues and impermeable polymeric or resinous membranes.

Various treatment regimens according to aspects of the present invention are contemplated. In one aspect, the administered active agent may provide an immediate therapeutic effect. In another aspect, the active agent may provide a sustained therapeutic effect. In yet another aspect, the active agent may provide an immediate therapeutic effect and a sustained therapeutic effect. In many cases, some form of sustained release may be beneficial in order to reduce the frequency of administration. Such a reduction in administration may increase patient compliance and reduce the frequency of eye infections and other related issues due to the decreased physical contact with the eye.

Various methods of providing sustained release, and therefore sustained therapeutic effect, are also contemplated, some of which have been discussed herein. Such a sustained release can be due to a property of the active agent, the use of a prodrug, the use of a sustained release depot, etc. In one aspect, a sustained release depot can be formed by the reaction of an active agent with a depot forming agent in the eye tissue, following delivery of the active agent to the subject. The depot forming agent can be delivered to the subject, or it can be an endogenous substance that reacts with the active agent. In either case, the depot forming agent and the active agent do not interact with one another until the active agent is delivered into the subject. As such, in most cases the active agent and the depot forming agent will be separated until both are located in-vivo. If the depot forming agent is to be delivered to the subject, then both agents should be delivered separately. Endogenous depot forming agents will, of course, not come into contact with the active agent until administration occurs. Thus an in-vivo reaction between the active agent and the depot forming agent will cause the active agent or a derivative thereof to form a depot. In one aspect such a depot forming mechanism may be a change in the solubility of the active agent or a derivative of the active agent, thus causing precipitation and subsequent depot formation. This depot of active agent complex is then able to deliver a therapeutic compound to the biological system over time. Such sustained delivery can include local or systemic delivery of the active agent to the subject.

As a sustained release mechanism, it will be recognized that a depot formulation generally has an in-vivo solubility that is lower than that of the active agent by itself. In this way, as the active agent dissolves out of the depot over time, a sustained therapeutic effect may be obtained. Further, since the active agent in the depot is unable to have a therapeutic effect until released therefrom, the solubility properties of the depot limit potential toxicity or overdose concerns that would normally arise when delivering a sufficient amount of drug to last over a prolonged period. Further details on such depot administration and depot agents can be found in U.S. patent application Ser. Nos. 11/238,144 and 11/238,104, both filed on Sep. 27, 2005, both of which are incorporated herein by reference.

It should be understood that the above-described arrangements are only illustrative of the application of the principles of the present invention. Numerous modifications and alternative arrangements may be devised by those skilled in the art without departing from the spirit and scope of the present invention. Thus, while the present invention has been described above with particularity and detail in connection with what is presently deemed to be the most practical and preferred embodiments of the invention, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A passive ocular active agent delivery device, comprising:
 a housing including a corneal region and a scleral region configured to couple to an eye of a subject;
 the corneal region comprising a corneal seal coupled to the housing and positioned in the housing to encircle a cornea of the eye during use, and to form the corneal region lacking a reservoir containing either an active agent or secondary compound therein;
 the scleral region comprising at least one active agent reservoir positioned to passively release active agent into the scleral region, wherein the scleral region is positioned over a sclera of the eye during use; and
 a pressure regulator coupled to the housing and operable to introduce negative pressure between the housing and the eye within the corneal region, wherein the corneal seal is operable to fluidically isolate the corneal region from the scleral region in response to the negative pressure.

2. The device of claim 1, wherein the pressure regulator is operable to introduce positive pressure between the housing and the corneal region of eye to facilitate release of the housing from the eye.

3. The device of claim 1, wherein the pressure regulator is a vacuum bulb.

4. The device of claim 1, wherein the pressure regulator is removably coupled to the housing.

5. The device of claim 1, further comprising a scleral seal coupled to the housing and positioned in the housing to encircle the corneal seal, the scleral region being between the corneal seal and the scleral seal.

6. The device of claim 5, wherein the scleral seal has a structure that is operable to preclude lachrymal fluid from entering the scleral region.

7. The device of claim 5, wherein the scleral seal is an outer edge of the housing.

8. The device of claim 5, wherein the pressure regulator is positioned in the housing to introduce the negative pressure into the scleral region.

9. The device of claim 1, further comprising a corneal cover coupled to the housing and extending inward from the corneal seal to completely cover the cornea during use.

10. The device of claim 1, wherein the pressure regulator is positioned in the housing to introduce the negative pressure into the corneal region.

11. A method of delivering an active agent to an eye of a subject while limiting the active agent from contacting an outer surface of a cornea during delivery, comprising:
   positioning the device of claim 1 on the eye of the subject;
   applying negative pressure between the housing and the eye to fluidically isolate the corneal region from the scleral region; and
   passively delivering an active agent to the scleral region, whereby the active agent is substantially precluded from the corneal region by the corneal seal.

12. A passive ocular active agent delivery device, comprising:
   a housing including a corneal region that is concentric within a scleral region, the housing configured to couple to an eye of a subject;
   the corneal region comprising a corneal seal coupled to the housing and positioned in the housing to encircle a cornea of the eye during use, and to form the corneal region lacking a reservoir containing either an active agent or secondary compound therein;
   the scleral region comprising at least one active agent reservoir positioned to passively release active agent into the scleral region, wherein the scleral region is positioned over a sclera of the eye during use; and
   a pressure regulator coupled to the housing and oriented off-center from a center of the housing and in fluid communication with the corneal region, said pressure regulator being operable to introduce negative pressure between the housing and the eye within the corneal region, wherein the corneal seal is operable to fluidically isolate the corneal region from the scleral region in response to the negative pressure.

13. The passive ocular active agent delivery device of claim 12, wherein negative pressure is applied between the housing and the eye in the scleral region.

14. The passive ocular active agent delivery device of claim 12, wherein the active agent reservoir has a surface area that is equal to 75% of the scleral region.

15. The passive ocular active agent delivery device of claim 12, wherein the active agent reservoir has a surface area that is equal to 10% of the scleral region.

16. The passive ocular active agent delivery device of claim 12, wherein the reservoir comprises an access port to allow the reservoir to be filled.

17. The passive ocular active agent delivery device of claim 12, wherein the pressure regulator is coupled to a pressure delivering channel that is operatively coupled to the corneal region.

* * * * *